United States Patent [19]

Veierov

[11] Patent Number: 6,001,874
[45] Date of Patent: Dec. 14, 1999

[54] ARTHROPOD CONTROL COMPOSITION FOR PLANT PROTECTION

[76] Inventor: Dan Veierov, P.O. Box 6, Bet-Dagan, Israel

[21] Appl. No.: 08/880,072

[22] Filed: Jun. 20, 1997

Related U.S. Application Data

[63] Continuation of application No. 08/107,891, Aug. 18, 1993, abandoned.

[30] Foreign Application Priority Data

Aug. 18, 1992 [IL] Israel ........................................ 102846

[51] Int. Cl.$^6$ .......................... A01N 27/00; A01N 31/00; A01N 35/00; A01N 35/06; A01N 37/02; A01N 37/04; A01N 37/06; A01N 65/00

[52] U.S. Cl. .......................... 514/533; 514/532; 514/544; 514/546; 514/547; 514/549; 514/552; 514/557; 514/558; 514/559; 514/560; 514/568; 514/572; 514/574; 514/675; 514/690; 514/691; 514/692; 514/693; 514/703; 514/724; 514/729; 514/730; 514/739; 514/762; 514/763; 514/764; 514/765; 514/766; 514/783; 514/786; 514/922; 514/946; 514/974; 424/195.1; 424/196.1; 504/110

[58] Field of Search ...................... 514/547, 558, 514/560, 724, 783, 786, 532, 533, 544, 546, 549, 552, 557, 559, 568, 572, 574, 675, 690, 691, 692–693, 703, 729, 730, 739, 762–766, 922, 946, 974; 424/195.1, 196.1; 504/110

[56] References Cited

U.S. PATENT DOCUMENTS

| | | | |
|---|---|---|---|
| 2,030,093 | 2/1936 | Bousquet et al. | 514/663 |
| 4,436,547 | 3/1984 | Sampson | 504/136 |
| 4,987,142 | 1/1991 | Tocker | 514/383 |
| 5,108,488 | 4/1992 | Etheridge | 504/130 |
| 5,631,290 | 5/1997 | Almond et al. | 514/560 |
| 5,741,502 | 4/1998 | Roberts | 424/405 |
| 5,756,773 | 5/1998 | Nagasampagi et al. | 549/383 |

FOREIGN PATENT DOCUMENTS

| | | |
|---|---|---|
| 53570 | 12/1977 | Israel . |
| 1272408 | 4/1972 | United Kingdom . |

OTHER PUBLICATIONS

"Repellents", D.A. Carlson, In: Kirk. Othmer Encyclo. Chem. Technol. pp. 785–805, 1978.
"Ecology and Metabolism of Plant Lipids", Glenn Fuller et al., American Chemical Society, 1987, pp. 220–238.
Combinations of Oils and Similar Compounds with Insecticides: Effect on Toxicity and Leaf Residues. L.S. Helser et al., South. Entomol.: pp. 75–81, 1986.
"The Residual Behavior of Fenpropathrin AD Chlorpyrifos Applied as Aqueous Emulsions and Oil Solution to Greenhouse Tomato Leaves", D. Veierov et al., Med. Fac. Landbouww, Gent 53: pp. 1535–1541, 1988.
W.S. Abbott, J. Econ. Entomol. 18, pp. 265–267, 1925.
CABA Abstract 92: 15375, abstracting Butler et al., "Effect of Oilsprays on Sweetpotato Whitefly . . .", Southwestern Entomologist, 1991, vol. 16 (1), pp. 63–72.
CABA Abstract 91: 4468, Abstracting Butler et al., "Cottonseed Oil and Safer Insecticidal Soap . . . " Southwestern Entomologist, 1990, vol. 15(3), pp. 257–264.
Veierov et al., "Optimization of Foliar Applied Formulations for the Control of the Tobacco Whitefly . . . " Final Report to U.S. Agency of International Development, 1991, p. 3.
Chemical Abstracts 100: 2207e (1984).

*Primary Examiner*—John Pak
*Attorney, Agent, or Firm*—Lowe, Hauptman, Gopstein, Gilman & Berner

[57] ABSTRACT

A non-toxic arthropod control composition is disclosed for application to foliage for plant protection. The composition includes behavior interfering compounds, agricultural oil and/or surface active compounds and diluents. The behavior interfering compounds may be any known conventional compound capable of interrupting or altering the normal behavioral sequences of the target. The agricultural oil can be a vegetable oil.

21 Claims, 1 Drawing Sheet

Effect of BIC+VO on field population of TWF (VO=3% cottonseed oil, BP=1% dibutyl phthalate, CAL=1% cetyl alc., LAI=1% lauryl alc.)

ARTHROPOD CONTROL COMPOSITION FOR PLANT PROTECTION

This application is a continuation of application Ser. No. 08/107,891 filed Aug. 18, 1993 now abandoned.

FIELD OF THE INVENTION

The present invention relates to arthropod control compositions for plant protection. More specifically said invention relates to non-toxic arthropod control composition applied to foliage for plant protection comprising a Behavior-interfering Compound, agricultural oil and/or surface active compounds and diluents.

BACKGROUND OF THE INVENTION

Biocompatible Insect Control-agents (herein called "BICs")—i.e. pest control agents which pose little hazard to humans and to the environment have been known for many years and their number is steadily growing. BIC can act as insect behavioral modifiers (such as feeding and oviposition detergents, repellents, etc.), hyperactivity inducers, knock down agents, physical barriers or physical poisons [J. J. Kabara (1987), Fatty Acids and Esters as Antimicrobial/insecticidal Agents. In G. Fuller and D. Nees (eds.): Ecology and Metabolism of Plant Lipids. Washington: ACS, pp. 220–238].

BIC are related to many chemical classes such as certain carboxylic acids, alcohols, esters, ethers, amides, terpenoids, limonoids, sulfides and heterocyclic compounds [D. A. Carlson (1978) Repellents. In: Kirk. Othmer Encyclo. Chem. Technol, pp. 786–805].

Increasingly, BIC are used as alternatives for neurotoxic insecticides mainly for human protection with (DE U.S. Pat. No. 3,211,632) and without (Carlson 1978) oils but also for veterinary purposes and to control food and store insects (IL Patent No. 53570).

Many BIC possess properties which are highly desirable also for plant protection, mainly on account of their rapid and safe action. However, most BIC cannot be applied to foliage due to their phytotoxic nature (Kabara 1987). One solution to this problem is to formulate BIC in a way which decreases their phytotoxicity and at the same time preserves or promotes their activity against the target pest.

The term agricultural oils [L. S. Helser and F. W. Plapp (1986) Combinations of Oils and Similar Compounds with Insecticides: Effect on Toxicity and Leaf Residues. South. Entomol.: 75–81] is used rather loosely to describe different mixtures of lipophilic chemicals [such as mineral oils, vegetable (corp) oils (hereinafter called "VO") and silicones], which differ enormously in their on-leaf behavior [D. Veierov, M. J. Berlinger and A. Fenigstein (1988), The Residual Behavior of Fenpropathrin and Chlorpyrifos Applied as Aqueous Emulsions and Oil Solution to Greenhouse Tomato Leaves. Med. Fac. Landbouww, Gent 53:1535–1541], Vegetable oils (VO) have been used for many years directly for control of weeds, fungi and insects, and as solvents and additives in conventional pesticide formulations.

Oils of various types were found to increase penetration of pesticides into leaf interiors (Veierov 1988). This, in part, explained the enhanced phytotoxicity of herbicides when applied to foliage together with oils.

Many types of VO can retard foliage penetration of pesticides when the two ingredients are properly formulated together. Moreover, the pesticide residue is retained above the leaf surface available to the insect and protected from weathering [D. Veierov and M. Ramakom (1991) Optimization of Foliar Applied Formulations for the Control of the Tobacco White Fly Under Field Conditions. Final Report to the U.S. Agency for International (AID) Development: 140].

BRIEF DESCRIPTION OF THE INVENTION

The present invention relates to a non-toxic arthropod control composition applied to foliage for plant protection comprising a Behavior-Interfering Compounds, agricultural oil and/or surface active compounds and diluents. The Behavior-Interfering Compound is any known conventional compound that can interrupt or alter the normal behavioral sequences of the target. The agricultural oil can be a vegetable oil.

DETAILED DESCRIPTION OF THE INVENTION

Figure 1:
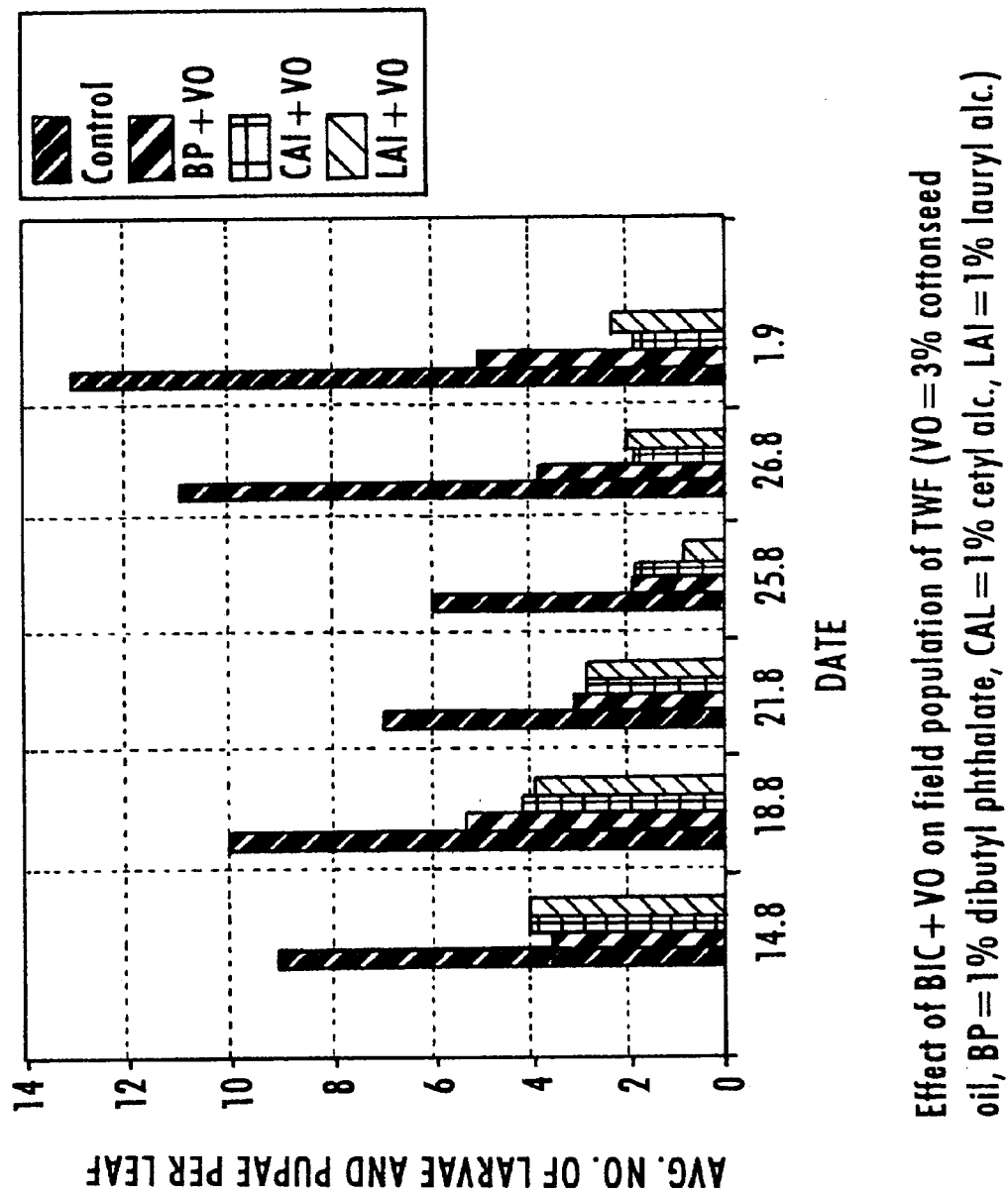
FIG. 1 is a graph depicting the ability of the three types of BIC+VO combinations to control field population of TWF.

The present invention relates to a non-toxic arthropod control composition applied to foliage for plant protection comprising a Behavior-Interfering Compounds, agricultural oil and/or surface active compounds (emulsifiers) and diluents (such as water or an appropriate organic solvents).

According to the present invention BICs phytotoxicity is masked and their efficacy is increased by formulating them with crop oils (agricultural oils) in the absence or presence of additional adjuvants.

Crop oils masks BIC phytotoxicity by reducing the contact between the BIC residue and leaf-surface, or by retarding BIC foliar penetration. The efficacy of BIC is promoted due to the action of the oil component as synergist and/or a complementary control measure. The oil component acts also as an extender.

Formulation of BIC with agricultural oil resulted in a very fast and persistant action, which is a prerequisite to control of some of the most serious types of agricultural pests.

Quick action is required to prevent the settling of migration stages of the target pest, and to deter egg deposition and/or virus transmission.

Persistent action guarantees prolonged protection both by repelling migrating stages and by killing the less mobiles ones (such as certain types of larvae).

In summary, BIC functions are: a) To provide fast activity as behavior modifiers, knock-down agents and/or physical barriers. b) To extend the effective doration of the oil residue.

Vegetable oil function: a) To reduce phytotoxicity. b) To synergies, or to provide complementary control activity. c) To extend BIC effective duration.

The BIC is any known conventional compound that can interrupt or alter the normal behavioral sequences of the target. The BIC can be any repellent or deterrent agent, hyperactivity inducer or irritant, narcotic, knock-down agent or physical barrier agent. Examples are $C_{10}$–$C_{22}$ alcohols, $C_{10}$–$C_{22}$ carbonyl compounds and terpenoids. More specifically the BIC is selected from methyl-nonyl ketone, N-butyl acetanilide, N,N-diethyl-3-methylbenzamide (DEET), dibutyl phthalate, dimethyl phthalate, dibutyl succinate, dibutyl adipate, butopyronoxyl (Indalone), butoxypoly (propylene glycol), benzyl benzoate, 2-ethyl-1,3-hexanediol, 2-butyl-2-ethyl-1,3-propanediol, 2-hydroxyethyl n-octyl sulfide, citronellal, camphor, camphene, terpinen-4-ol, linelool, isoborneol, borneol, isobornyl acetate, bornyl acetate, phytol, β-farnesene, lauryl alcohol, cetyl alcohol, oleyl alcohol, myristic acid, stearic acid.

The agricultural oil according to the present invention can be a vegetable oil. Said vegetable oil can be selected from cottonseed oil, soybean oil, rapeseed oil, castor oil, sunflower oil, groundnut oil, palm oil, safflower oil, coconut oil, sesame oil, corn oil and linseed oil.

The composition according to the present invention can be used against many types of arthropods e.g. sucking arthropods. Said composition can be applied against whiteflies (Aleurodides) and aphids (Aphidoidies).

The present invention relates also to a method for protection of plants against arthropod comprising application or spraying of the arthropod control composition defined in claim 1 to the plant leaves.

The invention will be clarified and exemplified by means of the following examples. Said examples are in no way intended to limit the scope of the invention.

FORMULATION EXAMPLES

Example 1 a) Emulsifiable concentrate (without co-solvent)

6–24 parts of active ingredient 88-70 parts of vegetable oil 6 parts of surfacetant (high hlb surfactant such as Tween 80 & Tween 20)

b) Emulsifiable concentrate (including co-solvent) 15 parts of active ingredient 41 parts of vegetable oil 41 parts of aromatic co-solvent (such as xylene)

3 parts of surfactant (preferably high hlb surfactant such as Tween 80 or Tween 20).

c) Emulsifiable concentrate (including co-solvent)

5 parts of active ingredient 16 parts of vegetable oil 78 parts of polar co-solvent (such as ethanol)

1 parts of surfactant (preferably high hlb surfactant such as Tween 80 or Tween 20).

By dilution of such a concentrate with water it is possible to prepare emulsions of the desired concentration which are especially suitable for leaf application.

d) Oil solution (for Ultra Low Volume spray)

1–3 parts of active ingredient

7–9 parts of vegetable oil

0–1 parts of surfactant (preferably high hlb surfactant such as Tween 80 or Tween 20)

BIOLOGICAL EXAMPLES: PHYTOTOXICITY TESTS

Example 2

Greenhouse test: The phytotoxicity of BIC+VO emulsions (examples 1a–d) was compared to that of emulsions of the separate components and to untreated controls. The emulsions were sprayed onto potted seedlings of cotton (Acala SJ-2) and tomato (Marmande) at the 4 leaf stage, and to pepper (Wyndal) and cucumber (Beit Alfa) at the 2 leaf stage. Sprays beyond runoff were made with hand-held sprayer at 4–6 psi. Discrete drops sprays (Ultra Low Volume, ULV) were applied with a commercial aerodynamic atomizer (Atomist, Root-Lowell Crcp., U.S.A.). To ensure LV-spray uniformity the potted plants were placed individually on a rotating table in front of the sprayer. The treated plants were held under greenhouse at average minimum and maximum temperatures were 15 and 22° C., respectively. Leaf damages were determined twice, 7 and 14 days post treatments. Individual leaves were visually assessed by averaging given samples, each consisting of ten potted plants. A rating of 0, 1, 2, 3, 4 indicated <1%, 1–10%, 11–25%, 26–50%, >50% average leaf damage respectively.

For all test plant species, treatments with BIC+VO formulations resulted in significantly lower level of foliar damage than treatment with BIC alone:

| | | Injury Indices on the Indicated Test Plants | | | | |
|---|---|---|---|---|---|---|
| Chemical[1] | Oil | Cotton | Tomato | Paper | Cucumber | Comments[2] |
| | | Esters | | | | |
| BP | (—) | 4 | 4 | 4 | | |
| BP | (—) | 4 | 4 | 4 | | ULV |
| BP | Cottonseed oil | 0 | 0 | 0 | | |
| BP | Cottonseed oil | 0 | 0 | 0 | | ULV |
| BP | Rapeseed oil | 0 | 0 | 0 | | |
| BP | Castor oil | 0 | 0 | 0 | | |
| BP | Soybean oil | 0 | 0 | 1 | | |
| BNBN | (—) | 4 | 4 | 4 | | |
| BNBN | (—) | 4 | | | | ULV |
| BNBN | Cottonseed oil | 0 | 1 | 1 | | |
| BNBN | Cottonseed oil | 0 | | | | ULV |
| BNBN | Rapeseed oil | 0 | 0 | | | |
| BNBN | Castor oil | 0 | 1 | 0 | | |
| BNBN | Soybean oil | 1 | 3 | 2 | | |
| | | Carboxylic acids | | | | |
| MAc | (—) | 0 | 2 | 2 | 3 | |
| MAc | Cottonseed oil | 0 | 0 | 0 | 0 | |
| MAc | Cottonseed oil | 0 | 0 | 0 | 0 | |
| MAc | Cottonseed oil | 0 | 0 | 0 | 0 | Ethanol |

-continued

| Chemical[1] | Oil | Injury Indices on the Indicated Test Plants | | | | Comments[2] |
|---|---|---|---|---|---|---|
| | | Cotton | Tomato | Paper | Cucumber | |
| MAc | Cottonseed oil | 0 | 1 | 0 | 1 | Xylene |
| MAc | Rapeseed oil | 0 | 0 | 0 | 0 | |
| SAc | (—) | 0 | 0 | 2 | 2 | Xylene |
| SAc | Cottonseed oil | 0 | 0 | 0 | 0 | Xylene |
| Fatty alcohols | | | | | | |
| CA1 | (—) | 0 | 1 | 2 | 2 | |
| CA1 | Cottonseed oil | 0 | 0 | 0 | 0 | |
| CA1 | Rapeseed oil | 0 | 0 | 0 | 0 | |
| CA1 | Soybean oil | 0 | 0 | 0 | 0 | |
| LA1 | (—) | 3 | 4 | 3 | | |
| LA1 | Cottonseed oil | 0 | 0 | 1 | | |
| LA1 | Rapessed oil | 0 | 0 | 0 | | |
| LA1 | Soybean oil | 2 | 3 | 2 | | |
| Terpenoids | | | | | | |
| TER. MIX. | (—) | 4 | 4 | | | |
| TER. MIX. | Cottonseed oil | 0 | 2 | | | Ethanol |
| TER. MIX. | Cottonseed oil | 0 | 1 | | | |
| 5\Miscellaneous | | | | | | |
| Deet | (—) | 4 | | | | |
| Deet | Castor oil | 1 | | | | |
| MGK-874 | (—) | 4 | | | | |
| MGK-874 | Castor oil | 1 | | | | |
| Oils & Untreated | | | | | | |
| (—) | (—) | 0 | 0 | 0 | 0 | |
| (—) | Cottonseed oil | 0 | 0 | 0 | 0 | |
| (—) | Rapessed oil | 0 | 0 | 0 | 0 | |
| (—) | Soybean oil | 0 | 0 | 0 | 0 | |
| (—) | Castor oil | 0 | 0 | 0 | | |

[1]BNBN = Benzyl benzoate,
BP = dibutyl phthalate,
CA1 = cetyl alcohol,
Deet (0.2%) = N,N-diethyl-m-toluamide,
LA1 = lauryl alcohol,
MGK-874 (0.2%) = 2-hydroxy-n-octyl sulfide,
MAc = myristic Acid,
SAc = Stearic acid,
TER. MIX = terpenoid mixture consists of Phytol (0.5%) + Linalool (0.25%) + Geraniol (1%) + Carvone (0.25%).
BIC concen. = 1% wt/wt, formulated with no co-solvent, if not specified otherwise.
[2]Ethanol = contains 3% ethanol,
LV = low volume spray,
Xylene = contains 3% xylens.

Example 3

Field test: Commercial cotton (H-23) was sown in regular row width (96.5 cm) during mid April 1991 in Kibbutz Ein-Hahoresh, Israel. Drip irrigation (385 m$^3$ water per 1000 m$^2$) and other standard agronomic practices were employed including insecticides sprays against moths and aphide (combination of Thionex 350 g/1000 m$^3$+Supracide 250 g/1000 m$^3$ on Jun. 21th, 1991 and Monooron 200 g/1000 m$^3$ on Sep. 6th, 1991). The plots were sprayed twice by BIC+ VO emulsions (on Aug. 8th and 14th, 1991) at 70 liter/1000 m$^3$ rate using portable mist blower.

Prior to the commercial harvest (Oct. 6th, 1991), 25 bolls were samples from the inner rows of each replicate and weighed and ginned. Lint quality was assessed by standard tests in the laboratories of the Cotton Production and Marketing Board Ltd., Herzellia, Israel. Foliar injuries assessed visually as described in Example 2.

No phytotoxic symptoms or significant changes in agronomic traits were found on plots treated with BIC+VO formulations compared to the control plots; plots treated with BIC alone suffered heavy foliar damage.

| Chemical[1] | Oil[2] | Injury Index | Boll Size (gr.) | Lint % | Sugars % | Homogeneity |
|---|---|---|---|---|---|---|
| Control | | 0 | 7.8 | 40.3 | 0.032 | 85.0 |
| (—) | Cottonseed oil | 0 | 7.0 | 39.8 | 0.026 | 86.2 |
| BP | (—) | 4 | (—) | (—) | (—) | (—) |
| BP | Cottonseed oil | 0 | 7.0 | 39.9 | 0.024 | 86.2 |
| CA1 | Cottonseed oil | 0 | 7.5 | 40.0 | 0.036 | 85.9 |
| LA1 | Cottonseed oil | 0 | 7.7 | 40.7 | 0.027 | 85.0 |
| Control | | 0 | | | | |
| (—) | Soybean oil | 0 | | | | |
| BP | (—) | 4 | | | | |
| BP | Soybean oil | 0 | | | | |
| CA1 | Soybean oil | 0 | | | | |
| LA1 | Soybean oil | 0 | | | | |

[1]1% wt/wt aqueous emulsion of
BP = dibutyl phthalate,
CA1 = cetyl alcohol,
LA1 = lauryl alcohol.
[2]Oil concentration = 3%.

BIOLOGICAL EXAMPLES: BIOACTIVITY TESTS

Example 4

Tobacco Whitefly adults response to various BIC: Tobacco Whitefly, (TWF, *Bemisia tabaci*) was reared on cotton seedlings in green house. Female whiteflies were caught with aspirator equipped with contraption, and transferred to clip-on leaf cage (transparent cylinder, base diameter 2 cm, height 7 cm).

The leaf cages, each containing twenty females, were attached to lower side of leaves of pre-treated cotton seedlings. The cotton seedlings had been sprayed to runoff with BIC and BIC+VO and held under controlled conditions for various aging intervals.

TWF settling and mortality were recorded after exposures of 1.5, 5 and 24 hr. Mortality results were corrected according to Abbott's formula [W. S. Abbott, J. Econ. Entomol. 18:265–267 (1925)]; settling deterrence was expressed as Settling Ratio (SR=[T/C], where T & C are the percentage of adults settled on treatment and control respectively after t hours of exposure). All experiments replicated 9–12 times.

A strong settling deterrence followed by death of TWF-adults were observed for the various BIC types. The activity of all combinations were stronger than those of each component separately (in several cases activity of BIC alone could not be measured due to severe leaf injuries).

| Chemical[1] | Settling Ratio (%) After the Indicated Exposure[2] | | Mortality (%) After the Indicated Exposure[2] | | Plant Injury |
|---|---|---|---|---|---|
| (% wt/wt) | 4 hrs. | 24 hrs. | 4 hrs. | 24 hrs. | Index[3] |
| Oil Alone | | | | | |
| CO | 20 | 62 | 0 | 37 | 0 |
| CO (4%) | 18 | 62 | 0 | 43 | 0 |
| Aromatic esters | | | | | |
| BP | (—) | (—) | (—) | (—) | 4 |
| BP + CO | 0 | 0 | 39 | 99 | |
| BNBN | (—) | (—) | (—) | (—) | 4 |
| BNBN + CO | 0 | 0 | 27 | 100 | |
| Aliphatic esters | | | | | |
| BS | 123 | 100 | 0 | 0 | 1 |
| BS + CO | 0 | 7 | 4 | 61 | 0 |
| Carboxylic acids | | | | | |
| MAc | 31 | 83 | 0 | 3 | 0 |
| MAc + CO | 0 | 12 | 3 | 56 | 0 |
| MAc + CA1 + CO | 1 | 2 | 12 | 72 | 0 |
| Fatty alcohols | | | | | |
| CA1 | 76 | 98 | 0 | 0 | 0 |
| CA1 + CO | 12 | 29 | 5 | 65 | 0 |
| CA1 + CO | 2 | 10 | 0 | 86 | 0 |
| Terpenoids | | | | | |
| TER. MIX. | (—) | (—) | (—) | (—) | 4 |
| TER. MIX. + CO | 15 | 17 | 26 | 76 | 0 |
| Camphene | 125 | 100 | | | 0 |
| Camphene + CO | 58 | 42 | 6 | 31 | 0 |
| Camphor + CO | 9 | 20 | (—) | 75 | 0 |
| Miscellaneous | | | | | |
| ETH | 83 | 97 | 0 | 0 | 4 |
| ETH + CO | 6 | 31 | 0 | 48 | 2 |

[1]Aqueous emulsions of
BNBN = benzyl benzoate,
BP = dibutyl phthalate,
BS = dibutyl sebacate,
CA1 - cetyl alcohol,
CO = cottonseed oil,
ETH = 2-Ethyl-1,3-hexanediol,
LA1 = lauryl alcohol,
MAc - myristic acid,
MAc + CA1 (0.5% of each),
OA1 = oleyl alcohol,
TER. MIX. = terpenoid mixture consists of Phytol (0.5%) + Linalool (0.25%) + Geraniol (1%) + Carvone (0.25%),
CO concen. = 3% and BIC concen. = 1% wt/wt, formulated with no co-solvent, if not specified otherwise.
[2]Three days post spray to cotton seedlings.
[3]A rating of 0, 1, 2, 3, 4 indicated <1%, 1–10%, 11–25%, 26–50%, >50% an average leaf damage.

Example 4: Continued (Responses of Tobacco Whitefly adults to various BIC)

| CHEMICALS[1] | SETTLING RATIO (%) AFTER[2] | | MORTALITY (%) AFTER[2] | | PLANT INJURY |
|---|---|---|---|---|---|
| (% wt/wt) | 4 h | 24 h | 4 h | 24 h | INDEX[3] |
| Carboxylic acids | | | | | |
| CIA | 100 | 93 | 0.5 | 2.8 | 0 |
| CIA + CO | 1.6 | 2.6 | 6.0 | 94 | 0 |
| MALE + CO | 34.8 | 8.3 | 34.4 | 86.6 | 0 |
| MALI + CO | 0 | 0.3 | 27 | 98.5 | 0 |
| SUCC + CO | 34.8 | 8.6 | 7.8 | 62.3 | 0 |

[1]CIA = citric acid,
MALE = Maleic acid,
MALI = malic acid,
SUCC = succinic acid,
CO = cottonseed oil,
CO concen. = 3% and BIC concen. = 1% wt/wt, formulated with no cosolvent, if not specified otherwise.
[2]Three days post spray to cotton seedlings.
[3]A rating of 0, 1, 2, 3, 4 indicated <1%, 1–10%, 11–25%, 25–50%, >50% an average leaf damage.

Example 5

TWF adults response to dibutyl phthalate in combination with various vegetable oils (VO): performed as described in Example 3.

The four vegetable oil+dibutyl phthalate combinations showed a very strong and persistent deterrence followed by death of TWF adults:

| Days Post-Spray | Oil type | Settling Ratio[2] (%) | | Mortality (%) | |
|---|---|---|---|---|---|
| | | Oil alone | Oil + BP | Oil alone | Oil + BP |
| 2 | Cottonseed | 1.1 | 0.0 | 69 | 99 |
| | Soybean | 2.0 | 0.0 | 91 | 100 |
| | Rapeseed | 2.3 | 0.0 | 72 | 100 |
| | Castor | 5.9 | 0.0 | 91 | 100 |
| 7 | Cottonseed | 85 | 7.3 | 15 | 75 |
| | Soybean | 90 | 12.3 | 6.8 | 69 |
| | Rapeseed | 0.0 | 0.0 | 83 | 100 |
| | Castor | 5.5 | 0.0 | 72 | 99 |
| 17 | Cottonseed | 84 | 7.0 | 0.9 | 37 |

-continued

| Days Post-Spray | Oil type | Settling Ratio[2] (%) Oil alone | Oil + BP | Mortality (%) Oil alone | Oil + BP |
|---|---|---|---|---|---|
| | Soybean | 90 | 12.0 | 0.0 | 56 |
| | Rapeseed | 5.3 | 0.0 | 54 | 98 |
| | Castor | 9.1 | 0.0 | 44 | 95 |

1 Aqueous emulsions of 3% oil and of 3% oil + 1% dibutyl pthalate.
[2]SR = (T/C), where T & C are the percentage of adults settled on treatment and control respectively.

Example 6

Responses of development stages of TWF to various BIC: Cotton seedlings sprayed with BIC combinations and with cottonseed oil and were held indoors (25° C.). A week postspray, leaf cages, each containing twenty females, were attached to lower leaf side for 24 hours. The number of eggs laid was counted under binocular microscope and compared with the control. The nymphs developing from the eggs, until the pupal stage, were counted 15–17 days after oviposition.

Seven-days old residues of CAl+CO and LAl+CO were active against developmental stages, whereas BP+CO residue was still active primarily against adults.

| Chemicals[1] | Mortality of Adults (%) | No. Eggs per Female | Relative No. Eggs per Female | Relative No. Pupae per Female | Relative No. Pupa Per Eggs |
|---|---|---|---|---|---|
| Control | 0 | 5.6 | 100 | 100 | 100 |
| CO (4%) | 15 | 4.2 | 75 | 39 | 52 |
| BP + CO | 91 | 0 | 0 | 0 | 0 |
| CA1 + CO | 15 | 2.5 | 45 | 7 | 16 |
| LA1 + CO | 4 | 4.7 | 75 | 15 | 20 |

[1]Aqueous emulsions of
CO = cottonseed oil,
BP = dibutyl phthalate,
CA1 = cetyl alcohol,
LA1 = lauryl alcohol,
Concentrations (% wt/wt) were CO = 3%, BIC = 1%, when not specified otherwise.

Example 6: Continued (Responses of development stages of TWF to various BIC)

| Chemicals[1] | Mortality of Adults (%) | No. Eggs Per Female | Relative No. Eggs Per Female (Con = 100%) | Relative No. Pupae Per Female (Con = 100%) | Relative No. Pupa Per Eggs (Con = 100%) |
|---|---|---|---|---|---|
| Non-treated | 0 | 4.7 | 100 | 100 | 100 |
| CO (4%) | 15 | 3.5 | 75 | 39 | 100 |
| CIA | 0 | 5.3 | 114 | 116 | 103 |
| CIA + CO | 90 | 0.2 | 4.5 | 3.3 | |
| MALE + CO | 87 | 0.1 | 3.0 | 0.6 | 20 |
| SUCC + CO | 62 | 0.2 | 6.0 | 6.0 | 100 |
| MMYR | 0 | 5.7 | 122 | 89 | 78 |
| MMYR + CO | 2 | 3.7 | 79 | 31 | 39 |

[1]Aqueous emulsions of
CO = cottonseed oil,
CIA = Citric Acid,

-continued

| Chemicals[1] | Mortality of Adults (%) | No. Eggs Per Female | Relative No. Eggs Per Female (Con = 100%) | Relative No. Pupae Per Female (Con = 100%) | Relative No. Pupa Per Eggs (Con = 100%) |
|---|---|---|---|---|---|

MALE = Maleic acid,
SUCC = succinic acid,
MMYR = methyl myristate
Concentrations (% wt/wt) were CO = 3%, BIC = 1%, when not specified otherwise.

Response of development stages of TWF to direct spray of various BIC

Cotton seedlings infected with a developmental stages of TWF were sprayed to runoff, after counting the eggs or the larvae presented. The plants were held under controlled conditions and the fraction of an immature stage developed into adults were measured and compared to that of the untreated control. The spray toxicity of BIC+OIL against various developmental stages of TWF is demonstrated in the following example.

| | % Survival of whitefly after direct spray of the indicated immature stage | | | | |
|---|---|---|---|---|---|
| Chemicals[1] | Egg | L1 | L2 | L3 | L4(P) |
| CO (4%) | 87 | 3.60 | 1.90 | 4.65 | 9.09 |
| LAL + CO | 49 | 0.00 | 0.28 | 0.00 | 0.74 |
| CAL + CO | 59 | 1.33 | 9.30 | 12.90 | 66.7 |
| SAL + CO | 93 | 0.74 | 0.27 | 0.22 | 13.0 |
| CAL + CO | 56 | 0.00 | 1.15 | 0.24 | 0.18 |

[1]Aqueous emulsions of:
CO = cottonseed oil,
LAL = lauryl alcohol,
CAL = cetyl alcohol,
SAL = stearyl alcohol,
OAL = oleyl alcohol.
Concentrations (% wt/wt) were CO = 3%, BIC = 1%, when not specified otherwise
[2]
L2 = 2nd instar nymph,
L3 = 3rd instar nymph,
L4 - 4th instar nymph (pupa)
[3]
$$\text{Survival} = \frac{[\text{fraction of a treated immature stage developed into adults}]}{[\text{fraction of an untreated immature stage developed into adults}]}$$

Example 7

Test of Dibutyl phthalate+VO combination as protectant against non-persistent virus transmitted by Aphids (*Myzue persicae*); Healthy cucumber seedlings (Beit Alfa) which served as a test plants were sprayed to runoff with BIC+VO combinations and allowed to dry. 1%-Virol spray was used as standard treatment. The control leaves were sprayed with surfactant solution. Aphid adults apterae (*Myzus persicae*), starved for 2 hours, were allowed 3 minutes access to untreated infected cucumber which served as a source for the non-persistent Zucchini Yellow Mosaic Virus (ZYMV). The aphids were subsequently confined for 24 hours on test plants by placing a tube around each test plant, and the survivors were killed. The test seedlings were allowed to grow until no more plants developed symptoms.

BIC+VO combination prevented completely the plant disease transmission, whereas VO emulsions and the standard mineral oil (Virol) sprays were less effective.

| | Transmission (%) | | Relative Transmission (%) (control = 100%) | |
|---|---|---|---|---|
| Oil type | Oil alone | Oil + BP | Oil alone | Oil + BP |
| Cottonseed | 24 | 0.0 | 40 | 0.0 |
| Soybean | 33 | 0.0 | 55 | 0.0 |
| Virol[1] | 36 | (-) | 60 | (-) |
| Control | 60 | (-) | 100 | (-) |

[1]1% - mineral oil applied as an aqueous emulsion (a standard treatment).

Example 8

Control of TWF under field conditions:; commercial cotton (H-23) was sown in regular row width (96.5 cm) during mid April 1991 in Kibbutz Ein-Hahoresh, Israel. Drip irrigation (385 m$^3$ water per 1000 m$^2$) and other standard agronomic practices except sprays against *Bemisiia tabaci* were employed.

Experimental plots were arranged in a randomized complete-block design with four replications per treatment. Each plot consisted of four rows X 12 m long with untreated plots separating replicates. The plots were sprayed twice by BIC+VO emulsions (on Aug. 8th and 14th, 1991) at 70 liter/1000 m$^3$ rate using portable mist blower. Leaf samples consisted of 10 leaves per replicate were collected the fifth node from the top of the main atom, twice a week started on Aug. 14th, 1991. Number of all living larvae and pupae (neonate excluded) on each samples leaf was determined by the aid of magnifying glass (x10).

The ability of the three types of BIC+VO combinations to control field population of TWF is demonstrated in FIG. 1.

I claim:

1. A method for controlling arthropods comprising the step of:
   applying to foliage a composition comprising (i) a Behavior Interfering Compound (BIC) selected from the group consisting of $C_{10-22}$ alcohols, $C_{10-22}$ carboxylic acids, terpenoids, esters of $C_{10-22}$ carboxylic acids, and esters of polybasic carboxylic acid, said BIC being present in a concentration of about 2% wt/wt or less, and (ii) a vegetable oil, said vegetable oil being present in a concentration of about 3% wt/wt or less, and which concentration of vegetable oil reduced phytotoxicity of said BIC.

2. The method of claim 1, wherein the BIC is selected from the group consisting of dibutyl phthalate, dimethyl phthalate, diethyl phthalate, dibutyl sebacate, dibutyl succinate, dibutyl adipate, citronellal, camphor, camphene, terpinen-4-ol, farnesol, geraniol, citral, terpineol, limonene, pinene, linalool, isoborneol, borneol, isobornyl acetate, bornyl acetate, phytol, lauryl alcohol, myristyl alcohol, stearyl alcohol, cetyl alcohol, oleyl alcohol, methyl myristate, myristic acis, stearic acid, and oleic acid.

3. The method of claim 1, wherein the BIC is a mixture of terpenoids comprising phytol, linalool, geraniol, and carvone.

4. The method of claim 1, wherein the vegetable oil is selected from the group consisting of cottonseed oil, soybean oil, rapseed oil, castor oil, sunflower oil, groundnut oil, palm oil, safflower oil, coconut oil, sesame oil, corn oil, tung oil, palm kernel oil, and linseed oil.

5. The method of claim 1, wherein the arthropod is a sucking arthropod.

6. The method of claim 5, wherein the sucking arthropod is selected from the group consisting of whiteflies and aphids.

7. The method of claim 1, wherein the arthropod is a soft-bodied organism.

8. The method of claim 7, wherein the soft-bodied arthropod is selected from the group consisting of mites, hoppers, mealy bugs and thrips.

9. The method of claim 1, wherein the composition is applied to leaves.

10. The method of claim 1, wherein the composition further comprises a surfactant or diluent.

11. The method of claim 10, wherein the surfactant is a high hlb surfactant.

12. The method of claim 10, wherein the diluent is water.

13. The method of claim 10, wherein the diluent is an organic solvent.

14. The method of claim 13, wherein the organic solvent is selected from the group consisting of an aromatic solvent and a polar solvent.

15. The method of claim 14, wherein the aromatic solvent is xylene.

16. The method of claim 14, wherein the polar solvent is ethanol.

17. The method of claim 1, wherein the foliage is from plants selected from the group consisting of cotton, tomato, pepper, and cucumber plants.

18. The method of claim 1, wherein said composition is formulated as a concentrate and diluted with water before application, the concentrate comprising:

6–24 parts BIC

70–88 parts vegetable oil 6 parts surfactant, wherein said dilution results in a composition with said BIC being present in a concentration of about 2% wt/wt or less, and with said vegetable oil being present in a concentration of about 3% wt/wt or less.

19. The method of claim 1, wherein said composition is formulated as a concentrate and diluted with water before application, the concentrate comprising:

15 parts BIC 41 parts vegetable oil 3 parts surfactant 41 parts diluent, wherein said dilution results in a composition with said BIC being present in a concentration of about 2% wt/wt or less, and with said vegetable oil being present in a concentration of about 3% wt/wt or less.

20. The method of claim 1, wherein said composition is formulated as a concentrate and diluted with water before application, the concentrate comprising:

5 parts BIC 16 parts vegetable oil 78 parts surfactant 1 parts diluent, wherein said dilution results in a composition with said BIC being present in a concentration of about 2% wt/wt or less, and with said vegetable oil being present in a concentration of about 3% wt/wt or less.

21. The method of claim 1, wherein said composition is formulated as a concentrate and diluted with water before application, the concentrate comprising:

1–3 parts BIC

7–9 parts vegetable oil

0–1 parts surfactant, wherein said dilution results in a composition with said BIC being present in a concentration of about 2% wt/wt or less, and with said vegetable oil being present in a concentration of about 3% wt/wt or less.

* * * * *